(12) United States Patent
Sabottke

(10) Patent No.: US 7,497,895 B2
(45) Date of Patent: Mar. 3, 2009

(54) MEMBRANE SEPARATION PROCESS

(75) Inventor: Craig Y. Sabottke, Baton Rouge, LA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 411 days.

(21) Appl. No.: 11/283,215

(22) Filed: Nov. 18, 2005

(65) Prior Publication Data

US 2007/0114177 A1 May 24, 2007

(51) Int. Cl.
*B01D 53/22* (2006.01)
*B01D 61/36* (2006.01)

(52) U.S. Cl. .................. 95/45; 95/46; 95/49; 95/50; 95/52; 95/54; 96/4; 210/640; 210/321.72; 210/188

(58) Field of Classification Search .............. 95/45, 95/46, 49, 50, 52, 54; 96/4; 210/640, 641, 210/650, 651, 321.6, 321.72, 188
See application file for complete search history.

(56) References Cited

U.S. PATENT DOCUMENTS

| | | | |
|---|---|---|---|
| 5,169,533 A * | 12/1992 | Baker et al. .................. 210/640 |
| 5,226,932 A * | 7/1993 | Prasad ............................. 95/45 |
| 5,236,474 A * | 8/1993 | Schofield et al. ............... 95/50 |
| 5,753,008 A | 5/1998 | Friesen et al. |
| 6,273,937 B1 * | 8/2001 | Schucker ........................ 95/50 |
| 6,866,698 B2 * | 3/2005 | Erickson et al. ................ 95/56 |
| 6,887,300 B2 * | 5/2005 | Nemser .......................... 95/45 |
| 2002/0139111 A1 | 10/2002 | Ueda et al. |
| 2005/0103710 A1 * | 5/2005 | Sabottke et al. ................ 95/45 |

FOREIGN PATENT DOCUMENTS

WO WO 2005/061422 A1 7/2005

* cited by examiner

*Primary Examiner*—Jason M Greene
(74) *Attorney, Agent, or Firm*—Lawrence E. Carter; Paul E. Purwin

(57) ABSTRACT

The invention relates to an improved membrane pervaporation and vapor permeation system in which the vacuum is produced by a fluid passing through a Venturi-type nozzle. The fluid is chosen from solvents that have little or no affinity for the permeate molecules. It is applicable over process feed rates, and can be used for the separation of aromatic species from hydrocarbon.

14 Claims, 4 Drawing Sheets

MEMBRANE SEPARATION PROCESS

FIELD OF THE INVENTION

The present invention relates to a method for the separation of a multi-component feed stream into a permeate stream rich in one or more components of the feed stream and a retentate stream lean in those same components.

BACKGROUND OF THE INVENTION

Pervaporation is a separation process where a membrane in contact with a multi-component liquid feed selectively absorbs one or more of the species from the feed. The sorbed species permeate across the membrane under the influence of a concentration gradient that is produced by evaporating the sorbed molecules from the product side of the membrane using a vacuum or sweep gas. Permeate vapor is then condensed and recovered as a liquid. Vapor permeation differs from pervaporation in that the feed is already in the vapor phase.

U.S. Pat. No. 5,753,008, incorporated by reference herein, discloses three ways for maintaining a sufficiently low partial pressure of permeate on the downstream side (also referred to as the "permeate side") of a membrane in a vapor permeation process: (a) by vacuum, (b) by dilution, and (c) by countercurrent sweep. When the low partial pressure is obtained by a vacuum or partial vacuum, it is conventional (i.e., known in the art of separations with polymer membranes) to use vacuum pumps and/or steam ejectors (including multi-stage steam ejectors).

While effective, vacuum pumps are expensive to maintain and can lead to difficulty in condensing the permeate. For this reason, pervaporation systems have been disclosed which use refrigeration equipment to assist in permeate condensation. Moreover, the vacuum pump oil may become contaminated with permeate, thus requiring more maintenance. And as a result of their generally low displacement, vacuum pumps are not typically useful in large separations systems.

While simpler, steam ejectors are limited in the level of vacuum they can achieve at reasonable steam flow rates. Consequently, staged ejectors are often needed for pervaporation separation systems. And since a small amount of permeate can remain in the steam condensate effluent, a treatment of the water effluent may be needed before discharge.

U.S. Pat. No. 6,273,937 attempts to overcome these difficulties by using a Venturi-type nozzle to produce the vacuum on the downstream side of the membrane. The Venturi is operated using a non-volatile working fluid that has an affinity for the permeate molecules. Since the working fluid has an affinity for the permeate molecules, the product effluent stream is heated and a flash drum is used to separate the permeate molecules, which can then be cooled and conducted away from the process. Following permeate separation in the flash drum, the non-volatile working fluid is cooled and pumped to the inlet of the Venturi for re-use. While the disclosed process achieves a vacuum on the downstream side of the membrane, it is complicated by the method selected to separate permeate from the Venturi effluent, as is also the case of the steam ejectors of U.S. Pat. No. 5,753,008.

There is, therefore, a need for a membrane separation process having an improved method for providing a vacuum on the downstream side of the membrane.

SUMMARY OF THE INVENTION

In an embodiment, the invention relates to a separation process, comprising:

(a) contacting a feed stream with a first surface of a permeation unit containing a membrane, with the feed stream containing at least a first species and a second species;

(b) selectively absorbing at least the first species into the first surface;

(c) selectively permeating at least the first species through the membrane from the first surface to an opposed second surface using a vacuum on the second surface in order to form a permeate rich in the first species and lean in the second species compared to the feed stream, the vacuum being produced by a fluid conducted through a Venturi nozzle, wherein the fluid comprises at least one solvent that is poorly miscible with the permeate;

(d) conducting the permeate from the second surface into the Venturi nozzle and into the fluid in order to form a Venturi effluent comprising at least a portion of the permeate and the fluid; and (e) separating the permeate from the fluid.

DETAILED DESCRIPTION OF THE INVENTION

The present invention relates to a method for the separation of a multi-component feed stream into a permeate stream rich in one or more components of the feed stream and a distinct retentate stream lean in those same components. More particularly, the present invention is directed to an improved method of achieving the vacuum required on the permeate side of the membrane using an aspirator such as a Venturi-type nozzle (or "Venturi") where the Venturi's working fluid has little or no affinity for the permeate. The invention can be understood by comparison to a conventional membrane separation process using a Venturi fluid that is immiscible with the permeate, as shown in FIG. 1.

Figure 1:
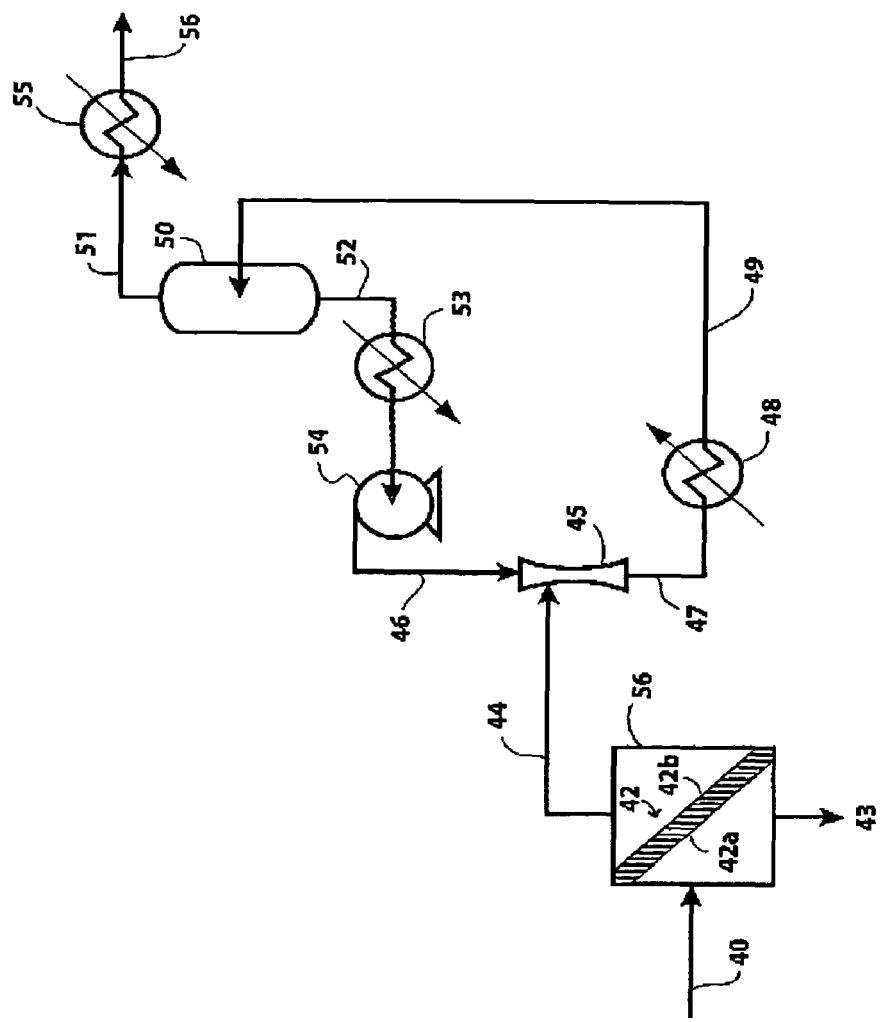
FIG. 1 schematically illustrates the flow of feed stream, permeate, and working fluid in a conventional membrane separation process.

In the conventional configuration shown in FIG. 1, the feed stream is pumped into a permeation unit 56 through line 40. The permeation unit contains a non-porous membrane 42 having a first surface 42a and an opposing second surface 42b. A portion of the feed dissolves into and permeates across the selective membrane 42 from the first surface 42a to the opposing second surface 42b. The permeate is volatilized from the second surface 42b by the vacuum produced by a Venturi nozzle 45 and exits the permeation unit through line 44. Venturi nozzles are conventional suction devices where, e.g., a converging-diverging pathway causes an increase in the velocity of flow of a working fluid and a corresponding decrease in fluid pressure, thus creating a suction, or vacuum, for drawing a fluid therethrough. Working fluid is pumped by pump 54 through line 46 into the Venturi nozzle. The passage of liquid through the converging-diverging nozzle creates a suction on the permeate module. Working fluid containing permeate exits through line 47 for heating by heat exchanger 48, and then passes through line 49 to the flash drum or tower 50, where the permeate flashes off and exits through line 51.

Permeate is then cooled and condensed by heat exchanger 55, which operates at approximately atmospheric pressure, and exits as a liquid through line 56. Non-volatile working fluid exits the flash tower through line 52, is cooled by heat exchanger 53, and enters the suction side of pump 54 for recycle to the Venturi-type nozzle.

The retentate exits the bottom of the permeation unit as 43 in FIG. 1.

Figure 2A:
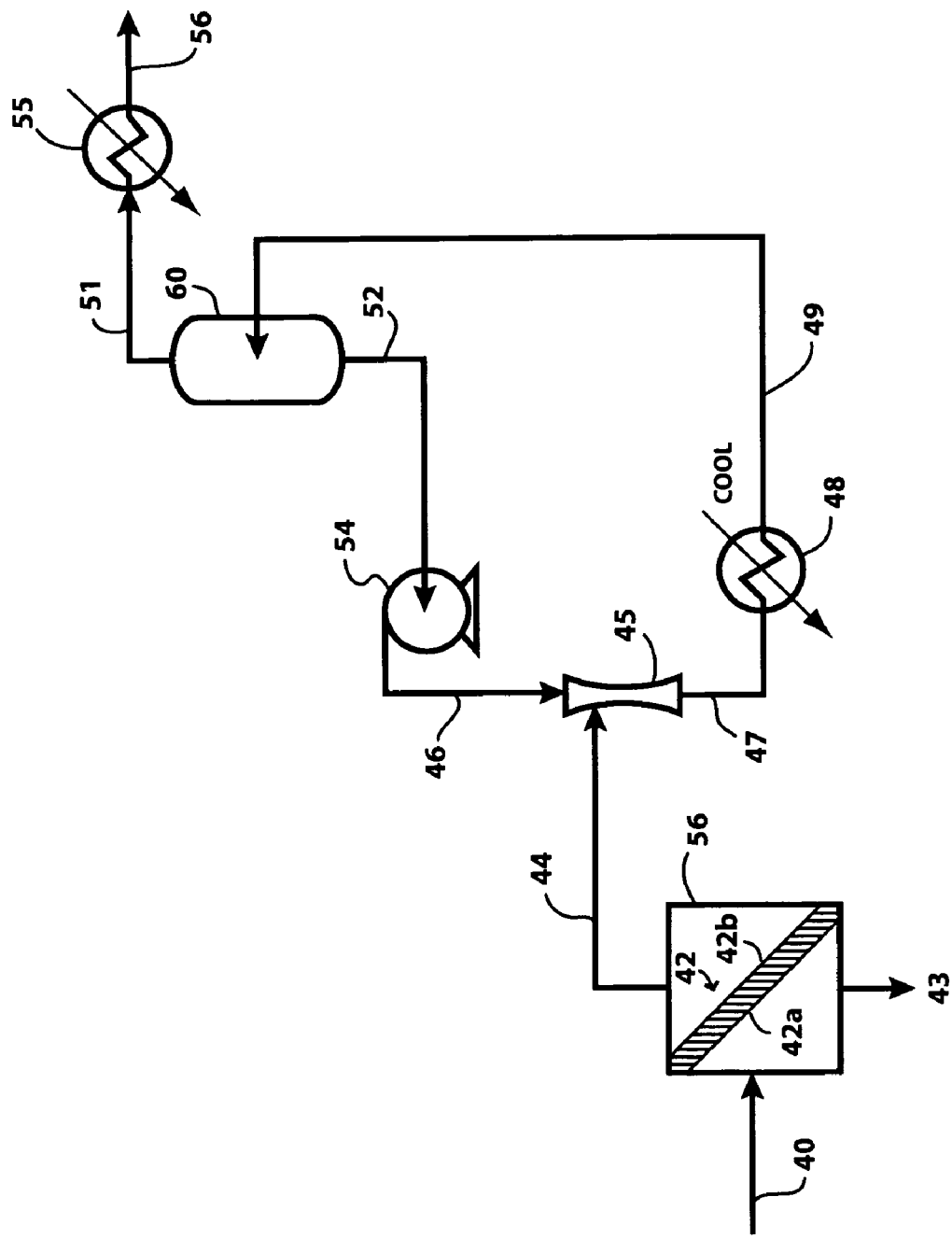
FIG. 2A schematically illustrates the flow of feed stream, permeate, and fluid in an embodiment of the invention, where the permeate is cooled downstream of the Venturi.

In an embodiment, the invention relates to the improved process illustrated schematically in FIG. 2A. The figure shows that a feed stream conducted to a permeation unit 56 through line 40. The permeation unit contains a non-porous membrane 42 having a first surface 42a and an opposing second surface 42b. A portion of the feed dissolves into and permeates across the selective membrane 42 from the first surface 42a to the opposing second surface 42b. The permeate is volatilized from the second surface 42b by the vacuum produced by a Venturi 45 and exits the permeation unit through line 44. Working fluid having little or no affinity for the permeate is pumped by pump 54 through line 46 into the Venturi nozzle. As in the conventional process, the passage of liquid through the converging-diverging nozzle creates a suction on the permeate module.

Figure 2B:
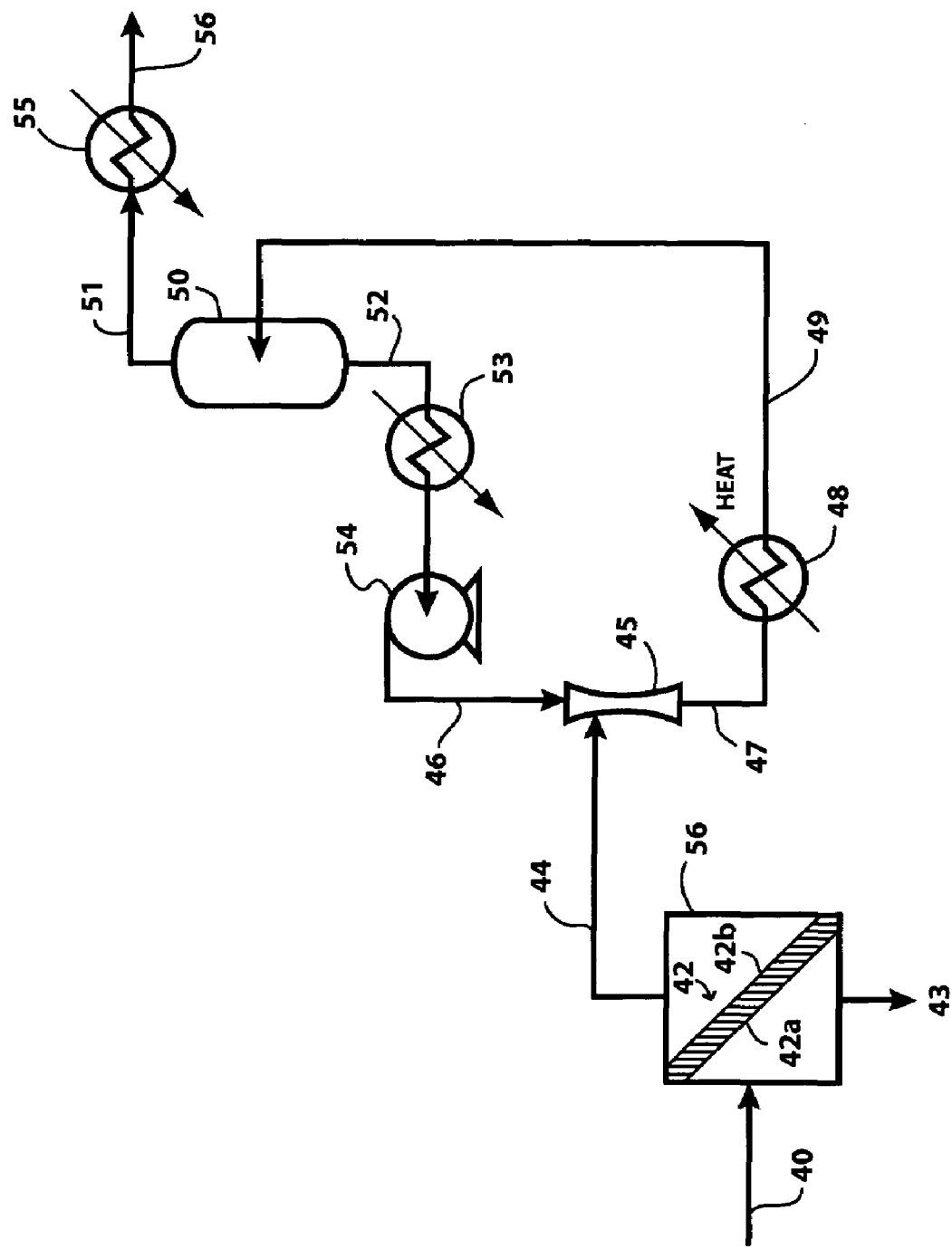
FIG. 2B schematically illustrates the flow of feed stream, permeante, and fluid in an embodiment of the invention, where permeate is heated downstream of the Venturi.

This embodiment differs from the conventional process in that the working fluid has little or no affinity for permeate molecules. Preferably, the working fluid and permeate are immiscible. Working fluid containing permeate is conducted away from the Venturi through line 47 to settling vessel 60. If the heat absorbed by the working fluid resulting from the introduction of hot permeate is sufficient to cause the working fluid to vaporize, then a heat exchanger 48 can be used to cool the working fluid back into the liquid phase. In an alternative embodiment, illustrated schematically in FIG. 2B, heat exchanger 48 is used to heat the working fluid. Since the working fluid and permeate are incompatible liquids, they will separate in the settling vessel (e.g., a conventional settling drum or tower) so that the permeate can be conducted away from the process. For example, when the permeate is aromatics and the working fluid is liquid water, the water will be present in the lower region of the settling tank and the aromatics will be present in the upper region, where they can be separated and conducted away from the process via line 56. While permeate can be cooled before it is conducted away from the process, it is an advantageous in an embodiment to conduct the permeate away without cooling, in contrast to the conventional process. Unlike the conventional process, this embodiment maintains the working fluid in the liquid phase, avoiding the need for cooling by heat exchanger 53. Accordingly, working fluid can be conducted away from settling vessel 60 directly to pump 54 for recycle and re-use by the Venturi.

Figure 3:
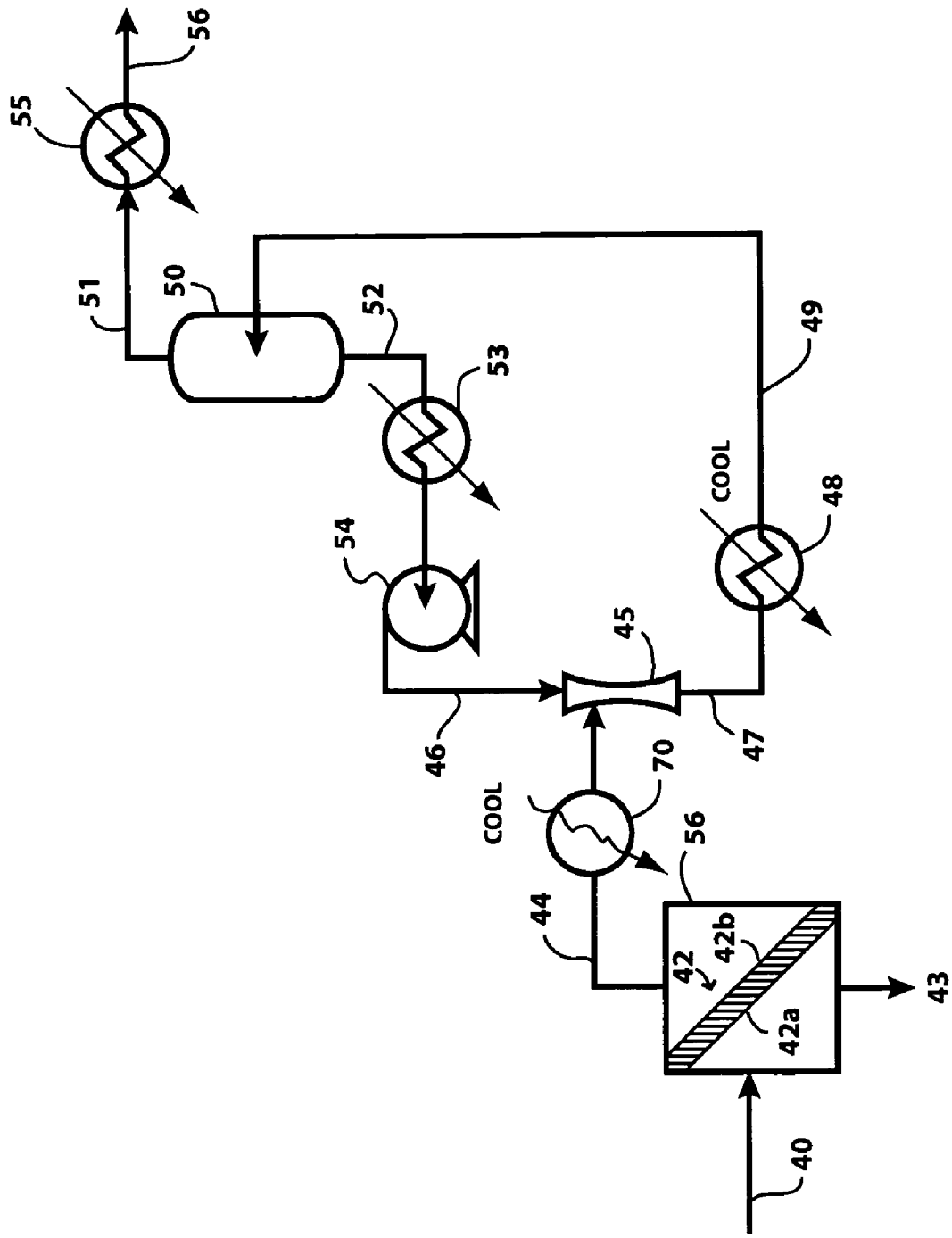
FIG. 3 schematically illustrates an embodiment where the permeate is partially condensed upstream of the Venturi.

In an embodiment, the invention relates to the improved process illustrated schematically in FIG. 3. The figure shows that a feed stream conducted to a permeation unit 56 through line 40. The permeation unit contains a non-porous membrane 42 having a first surface 42a and an opposing second surface 42b. A portion of the feed dissolves into and permeates across the selective membrane 42 from the first surface 42a to the opposing second surface 42b. The permeate is volatilized from the second surface 42b by the vacuum produced by a Venturi 45 and exits the permeation unit through line 44. The permeate is partially condensed through heat exchanger 70. Working fluid is pumped by pump 54 through line 46 into the Venturi nozzle. As in the conventional process, the passage of liquid through the converging-diverging nozzle creates a suction on the permeate module. In other respects, this embodiment is similar to the embodiments of FIGS. 2 and 3.

In a related embodiment, not illustrated, at least a portion of the working fluid in line 46 is diverted to the permeate side of the membrane unit 56 for use as a sweep fluid. In a preferred embodiment, the diverted portion of the working fluid from line 46 would be conducted to a let-down valve so that the diverted working fluid can be flashed and/or sprayed into the permeate zone of membrane unit 56 to provide additional permeate cooling. Hot vapor permeating away from membrane surface 42b is contacted and cooled by this sweep working fluid in the membrane unit 56 and line 44. The introduction of a suitable sweep fluid will increase the chemical potential driving force across the non-porous membrane 42. Increasing the chemical potential driving force for the separation improves the effectiveness of the separation.

The present invention provides a method of providing a vacuum for a pervaporation or vapor permeation system that does not use a vacuum pump or a steam ejector. It is based on the use of a converging-diverging (Venturi-type) nozzle that uses a liquid as the working fluid instead of steam. Examples of such nozzles include Venturis, eductors, and the like. The permeate side of the membrane module is connected directly to the throat of the Venturi, so that the working fluid passing through the nozzle pulls a vacuum on the membrane system.

The present invention can be used for both vapor permeation and pervaporation. It can be used in any number of separations, including hydrocarbon liquid separations, e.g., the separation of aromatics from a feed containing both aliphatic and aromatic species. Such streams can be obtained from, e.g., petroleum refining processes such as Fluid Catalytic Cracking (or "FCC") which produces a naphtha product ("cat naphtha") having an atmospheric boiling point ranging from about 75° F. to about 430° F.

Other separation processes applicable to the instant invention include (a) refinery separations including the separation of benzene from cat naphtha or gasoline and the separation of aromatics from lube oil streams; olefin/paraffin separation, such as ethylene from ethane and propylene from propane; and methyl tertiary butyl ether (MTBE)/methanol separation); (b) the recovery of volatile organic compounds from wastewater, such as MTBE from water; (c) the recovery of solvents from purge gas streams, which gas streams are preferably normally gaseous streams or permanent gas streams such as nitrogen, argon and the like, which can also include the recovery of trichloroethylene and other dry cleaning solvents from air; (d) alcohol/water separations, such as the removal of ethanol from water, including beverages; and (e) the dehydration of organic streams.

Preferred working fluids will have little or no affinity for permeate molecules and will be in the liquid state under process conditions. Unlike the conventional process, there is no need for the working fluid to have an effective boiling point different from the permeate boiling point. Preferably, the working fluid and the permeate will be immiscible or insoluble, and the working fluid will be chemically and thermal stability under process conditions.

By "little or no affinity" it is meant that the permeate and working fluid will be present as distinct physical phases. At the appropriate conditions, they will be distinct liquid phases. The term "immiscible" means the permeate and working fluid will be incapable of significant mixing and if allowed to reach an equilibrium condition will not attain homogeneity. Ranges of acceptable immiscibility are related to fluid surface tension and/or viscosity differences between the permeate fluid and working fluid. The minimum liquid surface tension ratio, defined as the working fluid surface tension divided by the permeate fluid surface tension should be greater than about 1.05. The minimum liquid viscosity ratio, defined as the working fluid viscosity divided by the permeate fluid viscosity, should be greater than about 1.05.

The term "insoluble" means the permeate and working fluid will be incapable of significant mixing and if allowed to reach an equilibrium condition will not attain homogeneity. Ranges of acceptable insolubility can be determined from data sources known to those skilled in the art. An example of a data source is the *Handbook of Chemistry and Physics*, 53$^{rd}$ Edition 1972-1973 published by the CRC Press. Sections covering pages C-53 to C-542 provide solubility information for various compounds relative to aromatic benzene. An example is compounds that are insoluble in aromatic benzene are also insoluble in aromatic permeate. Relative solubility to alcohols, water and other liquids is also detailed.

As an example, if the permeate is a petroleum naphtha then a working fluid derived from hydrocarbon, formate, glycol or silicon based chemistries that are capable of process operations between about −170° F. to about 650° F. and having suitable fluid surface tension and/or viscosity differences are acceptable.

By "gravity separation", it is meant that the liquid phase density difference between the permeate fluid density and working fluid density is different by at least greater than 10%. Conventional liquid-liquid gravity separation drums can be used to stabilize two distinct liquid phases. The lower density phase is the permeate fluid. The higher density phase is the working fluid. The lower density permeate fluid will stratify as the top liquid layer in a gravity separation drum. The higher density working fluid will settle as the bottom liquid layer in the gravity separation drum. Other density separation devices such as liquid centrifugal devices, stabilizing barrier media internal to settling drums and other devices known to those skilled in the art can also be used.

Working fluids for aromatic/aliphatic separations include fluids that are immiscible with hydrocarbon, such as water. Other examples of suitable working fluids for hydrocarbon separations include at least one of the following types of commercial heat transfer fluids derived from hydrocarbon, formate, glycol or silicon based chemistries that are capable of process operations between about −170° F. to about 650° F. Commercial products sold under the DOWTHERM brand name such as SLYTHERM 800, which is Dimethyl polysiloxane, are suitable working fluids. Other working fluids known to those skilled in the art can also be used.

Working fluids for recovery of VOCs from wastewater and recovery of solvents from gas streams include many of these same solvents and additionally include fluid derived from hydrocarbon, formate, glycol or silicon-based chemistries that are capable of process operations between about −170° F. to about 650° F.

For alcohol/water separations and dehydration of organic streams, working fluids include fluid derived from hydrocarbon, formate, glycol or silicon based chemistries that are capable of process operations between about −170° F. to about 650° F.

Persons of ordinary skill in the art will recognize that alternative separations processes and configurations would also be applicable to the invention, such as alternatives described in U.S. Pat. No. 6,273,937, incorporated by reference herein.

The invention claimed is:

1. A separation process, comprising:
   (a) contacting a feed stream with a first surface of a membrane unit containing at least one membrane, with the feed stream containing at least a first species and a second species;
   (b) selectively absorbing at least the first species into the first surface;
   (c) selectively permeating at least the first species through the membrane from the first surface to an opposed second surface using a vacuum on the second surface in order to form a permeate rich in the first species and lean in the second species compared to the feed stream, the vacuum being produced by a fluid conducted through a converging/diverging nozzle, wherein the fluid comprises at least one solvent that is poorly miscible with and/or of low solubility in the permeate;
   (d) conducting the permeate from the second surface into a heat exchanger whereby the permeate is partially condensed;
   (e) conducting the partially condensed permeate into the nozzle and into the fluid in order to form an effluent comprising at least a portion of the permeate and the fluid; and
   (f) separating the permeate from the fluid.

2. The process of claim 1 wherein the feed stream is a liquid.

3. The process of claim 2 wherein the feed stream comprises a naphtha stream which has a nominal boiling range of about 35° F. to about 450° F.

4. The process of claim 2 wherein the feed stream comprises a mixed gasoline stream.

5. The process of claim 2 wherein the feed stream comprises paraffins, olefins, and aromatics.

6. The process of claim 5 wherein the first species is aromatics.

7. The process of claim 6 wherein the second species is paraffin.

8. The process of claim 6 wherein the fluid comprises liquid water.

9. The process of claim 8 further comprising separating the permeate from the water by gravity separation in a settling vessel, conducting the separated permeate away from the process, and then recycling the water to the nozzle of step (c).

10. The process of claim 1 wherein said fluid is at least one of (i) water, and (ii) fluids derived from hydrocarbon, formate, glycol or silicon that are capable of process operations between about −170° F. to about 650° F.

11. The process of claim 1 further comprising diverting a portion of the fluid to the membrane unit proximate to the second surface in order to cool the permeate.

12. The process of claim 1 wherein the fluid is immiscible with and/or unsoluble in the permeate.

13. The process of claim 1 wherein the nozzle is a Venturi.

14. The process of claim 11, wherein the diverted portion of the fluid is flashed into the permeate zone.

* * * * *